(12) United States Patent
Ritter

(10) Patent No.: US 10,898,726 B2
(45) Date of Patent: Jan. 26, 2021

(54) PROVIDING AN ANNOTATED MEDICAL IMAGE DATA SET FOR A PATIENT'S RADIOTHERAPY PLANNING

(71) Applicant: Siemens Healthcare GmbH, Erlangen (DE)

(72) Inventor: Andre Ritter, Neunkirchen am Brand (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/574,262

(22) Filed: Sep. 18, 2019

(65) Prior Publication Data

US 2020/0094072 A1    Mar. 26, 2020

(30) Foreign Application Priority Data

Sep. 25, 2018 (DE) .......................... 10 2018 216 370

(51) Int. Cl.
*A61N 5/10* (2006.01)
*G16H 10/60* (2018.01)
(Continued)

(52) U.S. Cl.
CPC .......... *A61N 5/103* (2013.01); *A61N 5/1064* (2013.01); *G06T 7/0012* (2013.01); *G16H 10/60* (2018.01);
(Continued)

(58) Field of Classification Search
CPC ...... A61N 5/103; A61N 5/1064; G16H 10/60; G16H 30/20; G06T 7/0012
See application file for complete search history.

(56) References Cited

U.S. PATENT DOCUMENTS 9,135,686 B2 * 9/2015 Boyden ................. G06T 7/0012
10,191,921 B1 * 1/2019 Can ......................... G06N 3/08
(Continued)

FOREIGN PATENT DOCUMENTS

| CN | 101120871 A | 2/2008 |
|---|---|---|
| CN | 101779962 A | 7/2010 |
| EP | 3301649 A1 | 4/2018 |

OTHER PUBLICATIONS

Google Scholar Search Report.*
(Continued)

*Primary Examiner* — Qun Shen
(74) *Attorney, Agent, or Firm* — Harness, Dickey & Pierce, P.L.C.

(57) ABSTRACT

A method is for providing an annotated medical image data set for a patient's radiotherapy planning. In an embodiment, the method includes providing a planning image rule for the radiotherapy planning, including a scanning rule and a first reconstruction rule; retrieving an annotation rule from storage, containing annotation instructions and a second reconstruction rule, different from the first reconstruction rule; acquiring raw data of the patient in accordance with the scanning rule; reconstructing a first and second medical image data set in accordance with the first and second reconstruction rules using the raw data; annotating the second medical image data set in accordance with the annotation instructions, to determine annotated image information; combining the first medical image data set with the annotated image information, to produce the annotated medical image data set; and providing the annotated medical image data set for radiotherapy planning of the patient.

19 Claims, 3 Drawing Sheets

(51) Int. Cl.
    *G16H 30/20*     (2018.01)
    *G06T 7/00*     (2017.01)
    *G16H 30/40*     (2018.01)

(52) U.S. Cl.
    CPC ..... *G16H 30/20* (2018.01); *A61N 2005/1074* (2013.01); *G16H 30/40* (2018.01)

(56) References Cited

U.S. PATENT DOCUMENTS

| | | | | |
|---|---|---|---|---|
| 2007/0057211 | A1* | 3/2007 | Bahlman | G01N 21/6486 |
| | | | | 250/584 |
| 2014/0072192 | A1* | 3/2014 | Reiner | G06F 19/321 |
| | | | | 382/128 |
| 2015/0148652 | A1* | 5/2015 | Wanda | A61B 5/14542 |
| | | | | 600/407 |
| 2015/0221082 | A1* | 8/2015 | Carmi | G06K 9/52 |
| | | | | 382/128 |
| 2015/0297155 | A1* | 10/2015 | Christensen | A61B 6/4078 |
| | | | | 378/5 |
| 2016/0292874 | A1* | 10/2016 | Hsieh | G06T 11/008 |
| 2017/0091574 | A1 | 3/2017 | Udupa et al. | |
| 2017/0178349 | A1 | 6/2017 | Ketcha et al. | |
| 2017/0178365 | A1* | 6/2017 | Raupach | G06T 7/11 |
| 2018/0012382 | A1* | 1/2018 | Proksa | G06T 11/60 |
| 2018/0189604 | A1* | 7/2018 | Zhang | G06K 9/6262 |
| 2018/0315188 | A1* | 11/2018 | Tegzes | G06T 7/11 |
| 2018/0322254 | A1* | 11/2018 | Smurro | H04N 7/147 |
| 2019/0073803 | A1 | 3/2019 | Ritter | |

OTHER PUBLICATIONS

German Office Action for German Application No. 102018216370.7 dated May 3, 2019.
German Office Action and English translation thereof dated May 3, 2019.
German Decision to Grant and English translation thereof dated Feb. 10, 2020.
Egmont-Petersen Met Al: "Image processing with neural networks—a review", Pattern Recognition, Elsevier, GB, Bd. 35, Nr. 10, Oct. 1, 2002 (Oct. 1, 2002), pp. 2279-2301; XP004366785: ISSN: 0031-3203, DOI: 10.1016/S0031-3203(01)00178-9; 2002;.
Zhenghao Shi et al.: "Survey on Neural Networks Used for Medical Image Processing"; International journal of computational science, Feb. 1, 2009; (Feb. 1, 2009), pp. 86-100, XP055659028, China Gefunden im Internet URL:https://www.ncbi.nlm.nih.gov/pmc/articles/PMC4699299/pdf/nihms176967.pdf (gefunden am Jan. 17, 2020); 2009;.
Extended European Search Report dated Jan. 28, 2020.
Office Action for Chinese Patent Application No. 201910910385.8 dated Jul. 15, 2020.
Office Action for Chinese Patent Application No. 201910910385.8 dated Jul. 15, 2020 and English translation thereof.

* cited by examiner

PROVIDING AN ANNOTATED MEDICAL IMAGE DATA SET FOR A PATIENT'S RADIOTHERAPY PLANNING

PRIORITY STATEMENT

The present application hereby claims priority under 35 U.S.C. § 119 to German patent application number DE 102018216370.7 filed Sep. 25, 2018, the entire contents of which are hereby incorporated herein by reference.

FIELD

Embodiments of the invention generally relate to a method for providing an annotated medical image data set for a patient's radiotherapy planning, an associated medical imaging unit and an associated computer program product.

BACKGROUND

A patient's radiotherapy usually involves selective irradiation of a tumor, particularly for treating tumor-related diseases. The radiotherapy is usually carried out according to an irradiation pattern which may be very complex.

Radiotherapy planning comprises in particular determining the irradiation pattern and typically requires an annotated medical image data set which contains a planning image and annotated image information in a single medical image or in two separate medical images. Providing the annotated medical image data set is laborious and/or time-consuming particularly for a user of a medical imaging unit. A first requirement that the annotated medical image data set contains the planning image may conflict with a second requirement that the annotated medical image data set also contains the annotated image information.

SUMMARY

The inventors have discovered that to provide the annotated medical image data set, it may therefore be necessary in the case of consecutive imaging measurements, for raw data to be repeatedly acquired via the medical imaging unit in order to be able to meet the first requirement and the second requirement.

At least one embodiment of the present invention is directed to a method for providing an annotated medical image data set for a patient's radiotherapy planning, an associated medical imaging unit and an associated computer program product, wherein the planning image and the annotated image information can be provided after a single imaging measurement.

Advantageous embodiments are described in the claims.

The method according to at least one embodiment of the invention, for providing an annotated medical image data set for a patient's radiotherapy planning, comprises:

providing a planning image rule for radiotherapy planning, comprising a scanning rule and a first reconstruction rule, retrieving an annotation rule from a storage unit, wherein the annotation rule contains annotation instructions and a second reconstruction rule and wherein the second reconstruction rule is different from the first reconstruction rule, acquiring the patient's raw data via a medical imaging unit in accordance with the scanning rule, reconstructing a first medical image data set in accordance with the first reconstruction rule using the raw data, reconstructing a second medical image data set in accordance with the second reconstruction rule using the raw data, annotating the second medical image data set in accordance with the annotation instructions, wherein annotated image information is determined, combining the first medical image data set with the annotated image information, wherein an annotated medical image data set is produced, and providing the annotated medical image data set for the patient's radiotherapy planning.

The method according to at least one embodiment of the invention, for providing an annotated medical image data set for a patient's radiotherapy planning, comprises:

providing a planning image rule for the radiotherapy planning, including a scanning rule and a first reconstruction rule;

retrieving an annotation rule from storage, the annotation rule containing annotation instructions and a second reconstruction rule, the second reconstruction rule being different from the first reconstruction rule;

acquiring raw data of the patient via a medical imaging device in accordance with the scanning rule;

reconstructing a first medical image data set in accordance with the first reconstruction rule using the raw data acquired;

reconstructing a second medical image data set in accordance with the second reconstruction rule using the raw data acquired;

annotating the second medical image data set in accordance with the annotation instructions, to determine annotated image information;

combining the first medical image data set with the annotated image information, to produce the annotated medical image data set; and providing the annotated medical image data set for radiotherapy planning of the patient.

A medical imaging unit according to at least one embodiment of the invention comprises a processing unit, wherein the medical imaging unit is designed according to at least one embodiment of the method for providing the annotated medical image data set for the patient's radiotherapy planning. The processing unit typically comprises a processor, a network connection, the main memory and/or the buffer memory.

A medical imaging unit according to at least one embodiment of the invention comprises:

a memory storing executable instructions; and at least one processor, the at least one processor being, upon execution of the executable instructions, configured to:

provide a planning image rule for radiotherapy planning of a patient, including a scanning rule and a first reconstruction rule;

retrieve an annotation rule from storage, the annotation rule containing annotation instructions and a second reconstruction rule, the second reconstruction rule being different from the first reconstruction rule;

acquire raw data of the patient via a medical imaging device in accordance with the scanning rule;

reconstruct a first medical image data set in accordance with the first reconstruction rule using the raw data acquired;

reconstruct a second medical image data set in accordance with the second reconstruction rule using the raw data acquired;

annotate the second medical image data set in accordance with the annotation instructions, to determine annotated image information;

combine the first medical image data set with the annotated image information, to produce an annotated medical image data set; and provide the annotated medical image data set for radiotherapy planning of the patient.

A computer program product according to at least one embodiment of the invention, which can be loaded directly into a memory of the processing unit, has program code segments for carrying out at least one embodiment of the method for providing the annotated medical image data set for the patient's radiotherapy planning when the computer program product is executed in the processing unit.

In at least one embodiment of the invention, a computer program product is stored, for example, on a physical, computer-readable medium and/or in digital form as a data packet in a computer network. The computer program product can constitute the physical, computer-readable medium and/or the data packet in the computer network. Thus at least one embodiment of the invention can also proceed from the physical, computer-readable medium and/or the data packet in the computer network. The physical, computer-readable medium can usually be connected directly to the processing unit, e.g. by the physical, computer-readable medium being inserted in a DVD drive or plugged into a USB port, thereby providing the processing unit with, in particular, read access to the physical, computer-readable medium. The data packet can preferably be called up from the computer network. The computer network can contain the processing unit or be directly connected to the processing unit via a Wide Area Network (WAN) or a (Wireless) Local Area Network connection (WLAN or LAN). For example, the computer program product can be stored digitally on a cloud server at a storage location in the computer network, transferred via the WAN via the Internet and/or via the WLAN or LAN to the processing unit in particular by invoking a download link which indicates the storage location of the computer program product.

A non-transitory computer readable medium according to at least one embodiment of the invention, stores program code segments for, upon the program code segments being executed by the processor:

providing a planning image rule for radiotherapy planning of a patient, including a scanning rule and a first reconstruction rule;

retrieving an annotation rule from storage, the annotation rule containing annotation instructions and a second reconstruction rule, the second reconstruction rule being different from the first reconstruction rule;

acquiring raw data of the patient via a medical imaging device in accordance with the scanning rule;

reconstructing a first medical image data set in accordance with the first reconstruction rule using the raw data acquired;

reconstructing a second medical image data set in accordance with the second reconstruction rule using the raw data acquired;

annotating the second medical image data set in accordance with the annotation instructions, to determine annotated image information;

combining the first medical image data set with the annotated image information, to produce an annotated medical image data set; and providing the annotated medical image data set for the radiotherapy planning of the patient.

BRIEF DESCRIPTION OF THE DRAWINGS

The invention will now be described and explained in greater detail with reference to the example embodiments shown in the figures. In the following description of the figures, structures and units essentially remaining the same are always denoted by the same reference character as when the respective structure or unit first occurs.

DETAILED DESCRIPTION OF THE EXAMPLE EMBODIMENTS

Figure 1:
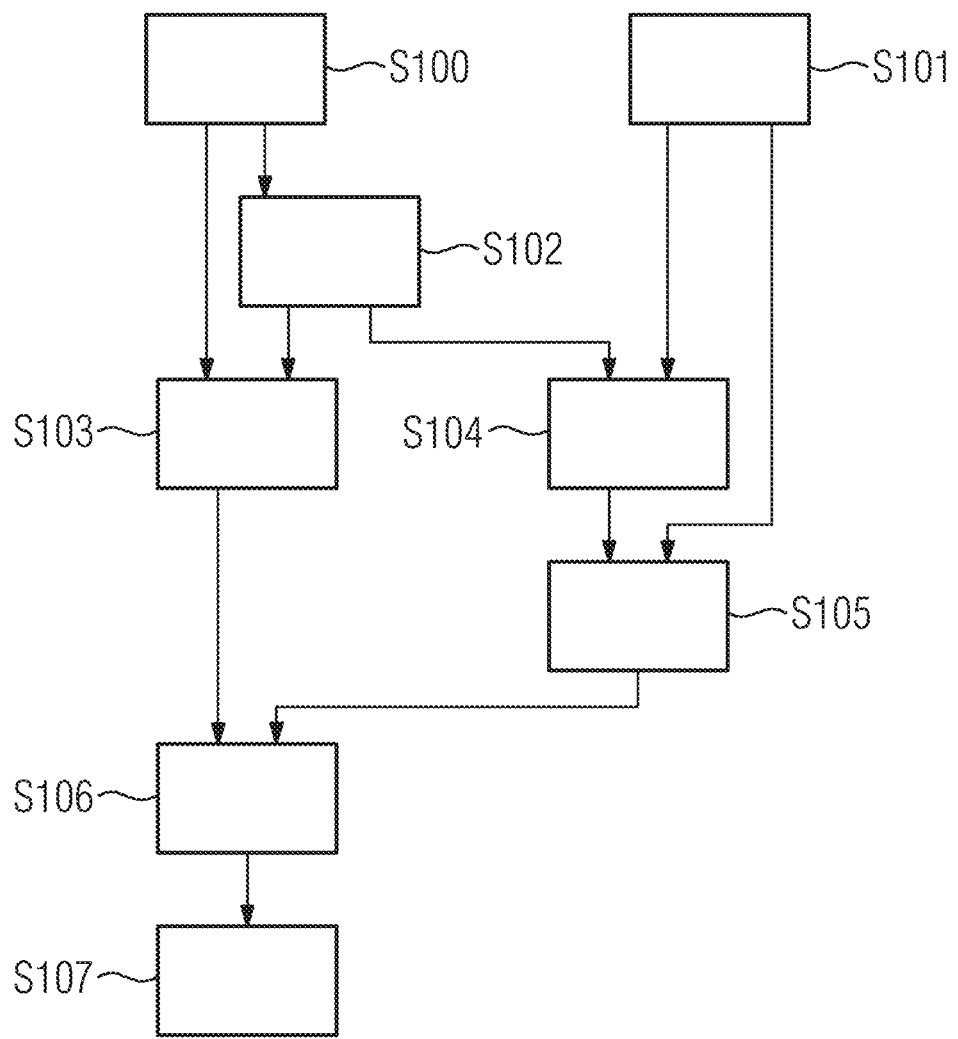
FIG. 1 shows a first example embodiment of a method for providing an annotated medical image data set for a patient's radiotherapy planning.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention, for providing an annotated medical image data set for a patient's radiotherapy planning, comprises:

providing a planning image rule for radiotherapy planning, comprising a scanning rule and a first reconstruction rule, retrieving an annotation rule from a storage unit, wherein the annotation rule contains annotation instructions and a second reconstruction rule and wherein the second reconstruction rule is different from the first reconstruction rule, acquiring the patient's raw data via a medical imaging unit in accordance with the scanning rule, reconstructing a first medical image data set in accordance with the first reconstruction rule using the raw data, reconstructing a second medical image data set in accordance with the second reconstruction rule using the raw data, annotating the second medical image data set in accordance with the annotation instructions, wherein annotated image information is determined, combining the first medical image data set with the annotated image information, wherein an annotated medical image data set is produced, and providing the annotated medical image data set for the patient's radiotherapy planning.

The method of at least one embodiment for providing the annotated medical image data set for the patient's radiotherapy planning has in particular, at least one of the following advantages:

Retrieval of the annotation rule from the storage unit preferably enables the annotated medical image data set to contain a planning image and annotated image information, wherein a user of the medical imaging unit can preferably merely provide the planning image rule. In other words, retrieval of the annotation rule from the storage unit eliminates workload for the user of the medical imaging unit, thereby typically providing cost savings. Alternatively or in addition, due to the fact that the annotation rule is retrieved from the storage unit and, in particular, is not provided by the user, a source of errors can thereby be eliminated. In particular, automatic retrieval of the annotation rule from the storage unit without user interaction is especially advantageous.

The annotated medical image data set advantageously contains the planning image and the annotated image information in high image quality, wherein ideally the irradiation pattern for radiotherapy planning can be determined in high quality and/or a conflict can be advantageously resolved. The conflict is in particular that a first requirement, wherein the annotated medical image data set contains the planning image, in particular in high image quality, precludes a second requirement, wherein the annotated medical image data set also contains the annotated image information, in particular in high image quality. The annotated medical image data set can preferably contain the planning image and the annotated image information without distorting the user's visual impression of the annotated medical image data set, particularly of the planning image.

Providing the annotated medical image data set, in particular the annotated image information together with the planning image, preferably enables additional user workload to be reduced because the annotated image information is already available and, in particular, does not need to be provided manually by the user. That is to say, for manual provision a conventional medical image data set would normally be used which can contain, for example, the planning image, but not simultaneously the annotated image information in high image quality unless in particular a plurality of imaging measurements are carried out. Preferably an average image quality of the annotated medical image data set is higher than an average image quality of the conventional medical image data set. Because the annotated medical image data set are provided in particular using the patient's raw data acquired in a single imaging measurement, further imaging measurements, in particular for providing the planning image and the annotated image information, can preferably be dispensed with, resulting in a reduction in costly examination time and/or X-ray dose.

Another advantage can be that in particular the providing of the annotated image information is standardized and/or comparable in respect of reference values because the annotation rule is retrieved from the storage unit. The annotated image information is preferably independent of the planning image rule provided, particularly of the first reconstruction rule. For example, the same annotation rule, but different planning image rules, can be used for a plurality of different patients. As a result, a high degree of comparability can be ensured, particularly in respect of annotated image information of the plurality of different patients.

The annotated medical image data set provided is particularly advantageous for automated radiotherapy planning for the patient, because automated radiotherapy planning normally uses standardized contouring and/or segmentation methods, which is made possible in particular by way of the standardized annotated image information. Alternatively or in addition, a clinically relevant structure of the patient can advantageously be provided more precisely using the annotated medical image data set than using the conventional medical image data set. Preferably the irradiation pattern determined by way of the annotated medical image data set is more precise and therefore more advantageous for the patient in respect of a prognosis and/or a treatment outcome and/or radiation exposure.

In different radiotherapy methods that are suitable for the patient's radiotherapy, in particular a plurality of types of ionizing radiation are used, e.g. gamma radiation, in particular as photon radiation, beta radiation, in particular as electron radiation, and/or in particle radiotherapy, hadron-based radiation, in particular as proton, neutron, He ion, alpha and/or carbon ion radiation. The different radiotherapy methods can usually be subdivided into internal radiotherapy methods or external radiotherapy methods. In the case of the external radiotherapy methods, the ionizing radiation is typically generated outside the patient, e.g. by way of radioactive isotopes and/or particle accelerator systems. In the case of the internal radiotherapy methods, a radiation source is usually introduced to generate the ionizing radiation in the patients, e.g. by way of a surgical and/or minimally invasive procedure.

Radiotherapy planning comprises in particular determining the irradiation pattern. For radiotherapy, the irradiation pattern is typically determined during radiotherapy planning. The irradiation pattern shows in particular a simulation via a spatially resolved radiation dose which in particular provides a prediction of the distribution of the ionizing radiation in the patient. The irradiation pattern describes in particular how the ionizing radiation is shaped by beam-shaping elements, in particular via multi-leaf collimators, and/or is administered to the patient from a plurality of directions. The irradiation pattern typically shows a target dose distribution and/or a maximum radiation dose distribution. The target dose distribution and/or the maximum radiation dose distribution are determined in particular by way of dose volume histograms, an average dose value, a minimum dose value and/or a maximum dose value, wherein in particular the planning image and the annotated image information are included as input parameters for the determination.

The target dose distribution defines in particular a minimum radiation dose in a clinically defined target volume, wherein in particular the annotated image information enables a clinically defined target volume to be delimited. The target volume contains in particular the patient's tumor to be treated and/or irradiated. The maximum radiation dose distribution defines in particular a maximum radiation dose outside the target volume, in particular in a healthy tissue, e.g. in an organ at risk. The maximum radiation dose can vary for different organs at risk. The radiotherapy is advantageously performed such that, in accordance with the irradiation pattern, the target dose distribution is achieved in the patient and the maximum radiation dose distribution is not exceeded. Some of the different radiotherapy methods preferably enable the target dose distribution to be a factor of 10 to 100 higher compared to the maximum radiation dose distribution.

Determining the irradiation pattern involves in particular determining the target dose distribution, e.g. the minimum radiation dose in the target volume, and/or the maximum radiation dose distribution, in particular the maximum radiation dose outside the target volume. Determining the irradiation pattern involves in particular performing the simulation via the spatially resolved radiation dose, wherein e.g. a Monte Carlo simulation is carried out. The irradiation pattern is usually determined in a radiotherapy planning system after the annotated medical image data set has been provided. The radiotherapy planning system can be part of the medical imaging unit or connected to the medical imaging unit, in particular via a radiology information system and/or a PACS picture archiving system, and/or provided via the processing unit. The user determines the irradiation pattern according to specifications of a radiation oncologist treating the patient. Alternatively or additionally, the irradiation pattern can be determined during automated radiotherapy planning.

Determining the irradiation pattern usually requires that the annotated medical image data set contains the planning image and the annotated image information. The annotated medical image data set in particular enables the irradiation pattern to be advantageously determined during radiotherapy planning. For determining the irradiation pattern, in particular the planning image and the annotated image information are provided together, because this enables in particular material properties, e.g. in the target volume, and/or the target volume to be taken into account.

The planning image preferably shows the material properties which can be used for simulation via the spatially resolved radiation dose, as the spatially resolved radiation dose usually depends on the material properties. The spatially resolved radiation dose can be calculated in particular by way of the planning image. The material properties typically include physical material properties of the patient. The planning image in particular enables pixel values of the annotated medical image data set to be converted into the material properties for calculating the spatially resolved radiation dose. The pixel values of the annotated medical image data set are converted in particular according to a conversion table. The pixel values can correspond to image values. The planning image and/or the annotated image information are in particular represented in the pixel values of the medical image data set. The pixel values of the medical image data set can be scaled e.g. according to a Hounsfield unit scale and/or other image value scales.

The annotated image information advantageously enables the target volume to be determined during radiotherapy planning. The annotated medical image data set preferably enables the target volume and/or the tissue outside the target volume to be contoured in particular by the user. The annotated image information can alternatively or additionally map a foreign body, in particular an implant, in the patient and/or a total patient volume. The contour of the target volume and/or of the tissue outside the target volume and/or of the foreign body can have, for example, at least one volume outer limit and/or an anatomical landmark. The annotated image information contains in particular the contour and/or the at least one volume outer limit.

The planning image rule for radiotherapy planning can be provided e.g. by the user of the medical imaging unit. The medical imaging unit can be, for example, a display unit and/or input device whereby the user provides the planning image rule. The planning image rule can be temporarily stored in particular in a main memory and/or in a buffer memory of the medical imaging unit. The planning image rule is in particular not stored in the storage unit. It is basically conceivable for the annotation rule to be retrieved from the storage unit and temporarily stored in the main memory and/or in the buffer memory together with the planning image rule. For acquiring the raw data, in particular the medical imaging unit can retrieve the planning image rule, in particular the scanning rule, from the main memory and/or the buffer memory. In particular for reconstructing the first medical image data set and/or the second medical image data set, a processing unit of the medical imaging unit can retrieve the planning image rule, in particular the first reconstruction rule, and/or the annotation rule, in particular the second reconstruction rule, from the main memory and/or the buffer memory. In particular for annotating the second medical image data set, the processing unit of the medical imaging unit can retrieve the annotation rule, in particular the annotation instructions, from the main memory and/or the buffer memory. It is basically conceivable for the processing unit to retrieve the annotation rule directly from the storage unit without the annotation rule being temporarily stored in the main memory and/or the buffer memory.

The annotation rule is in particular not provided by the user by way of the display unit and/or input device. In other words, providing the planning image rule typically does not involve providing the annotation rule. The annotation rule is typically retrieved from the storage unit independently of the user of the medical imaging unit, in particular independently of providing the planning image rule for the radiotherapy planning. The storage unit can be connected e.g. to the radiology information system and/or PACS picture archiving system which can in each case load the annotation rule into the storage unit e.g. when instructed by the processing unit so that it can be retrieved from the storage unit. It is basically conceivable for the annotation rule to be loaded into the storage unit by the manufacturer of the medical imaging unit, in particular prior to the medical imaging unit being provided in a hospital. The annotation rule can contain other reconstruction rules in addition to the second reconstruction rule, wherein, by way of the other reconstruction rules, further medical image data sets are reconstructed which can be used for annotating in accordance with the annotation instructions, wherein typically the annotated image information is determined.

Providing the planning image rule can include predefining the planning image rule, in particular predefining at least one and/or a plurality of parameters of the scanning rule and/or at least one and/or a plurality of reconstruction parameters of the first reconstruction rule. The scanning rule includes, for example, a tube current, a tube voltage, a measuring range and/or a duration of measurement. The scanning rule can alternatively or additionally include a rotation speed, a table feed during the imaging measurement, a table feed before and/or after the imaging measurement, a pitch in the case of a spiral imaging measurement and/or X-ray beam collimation. The scanning rule parameterizes in particular the imaging measurement during which the patient's raw data is typically acquired.

It is basically conceivable for the planning image rule to contain a physiological patient state rule, wherein the physiological patient state rule contains a cardiac phase and/or a respiratory phase of the patient and is taken into account for reconstructing the first medical image data set and for reconstructing the second medical image data set such that the first medical image data set and the second medical image data contain the physiological patient state rule. This is particularly advantageous because deformation of the patient typically depends on the physiological patient state, which means that in this case the work involved in combining the first medical image data set with the annotated image information can be reduced.

The first reconstruction rule and the second reconstruction rule typically differ in at least one reconstruction parameter of the following list:
in a slice thickness for the reconstruction,
in an inter-slice separation for the reconstruction,
in a reconstruction kernel,
in a reconstruction volume,
in an image value interval,
in an image value histogram,
in an iterative reconstruction method,
in an artifact correction method during reconstruction,
in a fidelity of reproduction of material properties that is determined during reconstruction.

The first reconstruction rule and the second reconstruction rule differ in particular in that a visual impression of the second medical image data set typically appears to the user as unsuitable compared to a visual impression of the first medical image data set. The second medical image data set can be optimized for annotation.

The image value histogram contains in particular a frequency distribution of the image values, e.g. in the target volume, of the first medical image data set and/or of the second medical image data set.

For example, the image value interval of the second medical image data set can be greater than the image value interval of the first medical image data set because the image value interval of the first medical image data set preferably renders the visual impression for the user that the user typically expects for radiotherapy planning, in particular in the planning image. The first medical image data set constitutes in particular the planning image. Annotation preferably takes place automatically, e.g. in the processing unit, for which the visual impression for user is typically irrelevant.

In the iterative reconstruction method, the first reconstruction rule and the second reconstruction rule can differ in that the first reconstruction rule is convolution-based, in particular without iterative reconstruction, and the second reconstruction rule involves iterative reconstruction or vice versa.

Alternatively or in addition, an iterative reconstruction parameter of the iterative reconstruction method can differ, in particular in an image space filter of the iterative reconstruction, in that the image space filter of the second reconstruction rule typically has spatially variable properties in contrast to the first reconstruction rule or vice versa, and/or in regularization of the iterative reconstruction. For example, the regularization of the iterative reconstruction method of the second reconstruction rule can be designed such that noise in the second medical image data set is preferably suppressed in a non-linear manner. In this case the second reconstruction rule can be designed such that the second medical image data set is optimized for annotation at the expense of a probability of detection of a particularly small anatomical structure. Alternatively, the second reconstruction rule can be designed such that in particular by way of the regularization the particularly small anatomical structure can preferably be precisely annotated. The iterative reconstruction method includes in particular a noise reduction method and/or a non-linear image filter. Whether the particularly small anatomical structure is not detected or is precisely detected, can depend on the clinical objective.

The patient's raw data is typically acquired during the imaging measurement. To acquire the raw data, the imaging measurement is in particular carried out once. The raw data is e.g. projection data, if the medical imaging unit comprises a computed tomography scanner, or k-space data, if the medical imaging unit comprises a magnetic resonance imaging scanner. It is conceivable for the medical imaging unit to have a combination of computed tomography scanner, magnetic resonance imaging scanner, positron emission tomography scanner and/or single photon emission computed tomography scanner.

After acquisition, the raw data can be temporarily stored e.g. in the main memory and/or the buffer memory and/or transferred to the radiology information system and/or the PACS picture archiving system. Acquiring the raw data may involve injecting a contrast agent into the patient. The raw data represents in particular the measuring range. The measuring range can correspond to a maximum field of view which typically includes a tunnel-shaped aperture of the medical imaging unit. The measuring range can alternatively be defined such that raw data can preferably be acquired over an angular range of at least 180° for each point within the measuring range. The measuring range can completely or partially fill out the maximum field of view. The measuring range is typically smaller or of equal size or greater in comparison to the reconstruction volume of the first reconstruction rule and/or to the reconstruction volume of the second reconstruction rule. Particularly for radiotherapy planning, the measuring range can be smaller because the first reconstruction rule and/or the second reconstruction rule are designed to extrapolate the raw data in a region outside the measuring range. The raw data is usually not provided by the user on the display unit.

The first medical image data set and/or the second medical image data set are usually reconstructed in the processing unit of the medical imaging unit, e.g. in any sequence or in parallel. The first medical image data set and/or the second medical image data set and/or the annotated medical image data set can be transferred to the radiology information system and/or the PACS picture archiving system and/or provided on the display unit. The first medical image data set and/or the second medical image data set and/or the annotated medical image data set have at least one image data set dimension. It is conceivable that four image data set dimensions describe the measuring range using three image data set dimensions and a time dimension as the fourth image data set dimension.

Annotation can involve aggregating functional information of the patient. The annotating is based in particular on a contrast in the second medical image data set. The annotating can be carried out taking into account the absolute pixel values and/or the pixel values relative to one another using the second medical image data set. The annotation instructions are in particular designed such that annotation involves segmenting, classifying and/or identifying in the second medical image data set. Segmentation describes in particular a delimitation, classification typically an assignment to categories and/or identification usually recognition. The categories may differentiate e.g. between vital tissue, diseased tissue, functional tissue, neovascular tissue and/or necrotic tissue. Identifying a tumor type is advantageous particularly in respect of selecting the radiotherapy method, because resistances to the ionizing radiation can depend on the type of tumor. The annotation can relate in particular to a morphology and/or an anatomy and/or the clinically relevant structure of the patient and/or the implant and/or the anatomical landmark. The tumor can in particular contain a plurality of metastases. The clinically relevant structure can in particular describe a pulmonary nodule and/or a lymph node. Alternatively or in addition, annotation can include modeling of the anatomy, of the clinically relevant structure of the patient, of the implant and/or of the anatomical landmark in a mathematically parameterizable formal model. The modeling includes in particular minimizing a distance dimension.

It is basically conceivable for annotation to involve selecting an annotated medical image data set, e.g. from the radiology information system and/or the PACS picture archiving system, which comparison shows to have a high degree of similarity to the second medical image data set. In this case, annotated image information of the annotated medical image data set selected is typically registered onto the second medical image data set, wherein the annotated image information of the second medical image data set is determined.

The annotating of the second medical image data set can include extracting radiomics features. The radiomics features include in particular a measure extracted from the second medical image data set, in particular a shape, an image value distribution and/or a texture of the pixel values in particular of the target volume and/or of the tissue outside the target volume.

The annotation instructions include in particular image processing instructions and/or can in particular be represented in annotation program code segments. The annotation instructions include in particular a pattern recognition and/or an image recognition algorithm. The annotating takes place e.g. in the processing unit in which the annotation program code segments are executed.

The annotated image information is typically present in a data structure. The annotated image information comprises in particular a binary mask, a probability mask, a grid structure, a polygonal line, vertices of a polygon and/or labeling. The annotated image information is typically present relative to a coordinate system of the second medical image data set and/or can be sorted slice by slice.

The second medical image data set is typically discarded after the annotated image information has been determined, in particular after the annotated medical image data set has been generated. In other words, the annotated medical image data set generated typically includes the first medical image data set, the annotated image information, and not the second medical image data set.

The combining involves, for example, the annotated image information being transferred from the second medical image data set to the first medical image data set, in particular using the processing unit, wherein typically a coordinate system of the first medical image data set and a coordinate system of the second medical image data set can be matched to one another. The combining involves, in particular, registering and/or modeling and/or interpolating and/or extrapolating the first medical image data set and/or the annotated image information and/or the second medical image data set with the annotated image information.

The annotated medical image data set is available, for example, in DICOM image format. The first medical image data set is stored e.g. as image information of the DICOM image format and/or the annotated image information, in particular the data structure, is stored as data information of the DICOM image format. It is basically conceivable for the annotated image information in addition to the first medical image data set to be stored as the image information of the DICOM image format. For example, the annotated image information can be overlaid on the first medical image data set. Generating the annotated medical image data set involves in particular generating a segmented medical image data set, a classified medical image data set, an identified medical image data set and/or a modeled medical image data set.

The annotated medical image data set is available, for example, in a DICOM image format file. It is conceivable for the annotated medical image data set to comprise a plurality of files, wherein e.g. a first file contains the first medical image data set and a second file the annotated image information. The first file and/or the second file can be available in DICOM image format and/or in another image format. It is basically conceivable that for each slice, e.g. for each medical image with two image data set dimensions, of the annotated medical image data set, a file with the slice-related planning image and with the slice-related annotated image information or for each slice two files, with in each case the slice-related planning image and the slice-related annotated image information, are created.

The annotated medical image data set can be provided, for example, on a data medium and/or on the display unit and/or in the radiology information system and/or in the PACS picture archiving system and/or on the radiotherapy planning system. The radiotherapy planning system can include the display unit and/or the input device. The radiotherapy planning system can be part of the medical imaging unit or be disposed outside the medical imaging unit. The medical imaging unit is connected to the radiotherapy planning system e.g. via a network and/or the radiology information system and/or the PACS picture archiving system. The display unit can be implemented as part of an image processing workstation. The radiotherapy planning and/or the radiotherapy are typically performed after the annotated medical image data set has been provided.

An embodiment provides that an artifact correction method of the first reconstruction rule differs from an artifact correction method of the second reconstruction rule in that, after using the artifact correction method, the number of image artifacts in the second medical image data set is less than the number of image artifacts in the first medical image data set. The artifact correction method comprises in particular a method for reducing beam-hardening and/or metal artifacts. The artifact correction method of the first reconstruction rule can in particular be deselected by the user when providing the planning image rule. Using the artifact correction method, in particular of the first reconstruction rule, can distort the visual impression for the user. Irrespective of the visual impression for the user, the number of image artifacts in the second medical image data set can preferably be reduced compared to the first medical image data set.

An embodiment provides that a fidelity of reproduction of material properties of the first reconstruction rule is higher than a fidelity of reproduction of the material properties of the second reconstruction rule. The first medical image data set preferably reproduces the material properties more precisely than the second medical image data set. Advantageously, the first medical image data set, in particular the planning image, can reproduce the material properties more precisely than the second medical image data set.

An embodiment provides that a slice thickness of the second reconstruction rule is less than a slice thickness of the first reconstruction rule. Typically an information loss, e.g. because of a disadvantageous fulfillment of a sampling theorem, can be prevented. When providing the planning image rule, the user typically selects a comparatively large slice thickness, e.g. 4 mm, as the slice thickness of the first reconstruction rule, whereas the slice thickness of the second reconstruction rule is smaller, in particular 3 mm, advantageously 2 mm, particularly advantageously 1 mm.

An embodiment provides that a reconstruction volume of the second reconstruction rule is greater than a reconstruction volume of the first reconstruction rule. The reconstruction volume of the second reconstruction rule can completely or partially fill up the measuring range. The reconstruction volume of the second reconstruction rule can completely encompass e.g. the target volume and/or the organ at risk, whereas the reconstruction volume of the first reconstruction rule is in particular defined by the user such that information can be lost particularly at edge positions. For example, it is more advantageous for annotating if the reconstruction volume completely encompasses the target volume and/or the organ at risk. The reconstruction volume of the second reconstruction rule can preferably be more than 5%, advantageously 10% and/or particularly advantageously 15% larger than the reconstruction volume of the first reconstruction rule.

An embodiment provides that the first reconstruction rule differs from the second reconstruction rule in that an image resolution in the second medical image data set is higher than an image resolution in the first medical image data set. In this case the annotating can be performed more precisely because the second medical image data set preferably contains more image information than the first medical image data set for which image information may typically be averaged because of the reduced image resolution. The image resolution of the second medical image data set can be a factor of 1.05, advantageously a factor of 2 and particularly advantageously a factor of 4 greater than the image resolution of the first medical image data set.

An embodiment provides that a filter of the second reconstruction rule differs from a filter of the first reconstruction rule in that image edges in the second medical image data set are represented in a more contoured manner than image edges in the first medical image data set. The filter of the second reconstruction rule is in particular optimized such that in particular anatomical and/or morphological edges are better accentuated in the second medical image data set. The image edges can in particular represent the anatomical edges and/or the morphological edges. The filter of the second reconstruction rule can in particular comprise a median filter. The filter of the first reconstruction rule can comprise in particular a mean value filter which typically produces less distortion of the visual impression for the user. The filter describes in particular an optimizing of image values and/or of image noise. The image edges are in particular represented in a more contoured manner if the pixel values which map the image edges are spaced farther apart relative to one another.

An embodiment provides that the second reconstruction rule contains reference value specifications, wherein the reference value specifications are taken into account for reconstructing the second medical image data set, whereby a contrast of the first medical image data set differs from a contrast of the second medical image data set. The reference value specifications in particular enable the providing of the annotated image information to be standardized, whereby in particular the standardized annotated image information is provided. The reference value specifications are particularly advantageous for automated radiotherapy planning. For example, the reference value specifications can stipulate that the second medical image data set contains a visual impression of a tube voltage other than that which the tube voltage used for acquiring the raw data can provide. The contrast comprises in particular a representation of the image edges in pixel values. The contrast depends in particular on a spectral weighting of the raw data.

An embodiment provides that the reference value specifications include a CT number for an organ of the patient. The reference value specifications can correspond, for example, to an imaginary reference patient. In this embodiment, for example, the second medical image data set can be reconstructed such that the patient's organ has the CT number and/or a slight deviation from the CT number, which can be advantageous in particular for automatic radiotherapy planning. The patient's organ can be e.g. the patient's liver, wherein in this case the CT number can be between 50 and 100 HU, advantageously between 70 and 90 HU, preferably between 75 and 85 HU and/or with particular preference 80 HU.

An embodiment provides that the scanning rule includes a multi-energy scanning rule for acquiring spectrally resolved raw data and wherein the first reconstruction rule differs from the second reconstruction rule in respect of weighting of the spectrally resolved raw data. The multi-energy scanning rule can include a dual-energy measurement. For example, the second reconstruction rule can be designed such that the annotating in particular delivers better results because of the weighting of the spectrally resolved raw data.

An embodiment provides that the first reconstruction rule differs from the second reconstruction rule in that the first medical image data set and the second medical image data set have different image data set dimensions. For example, it can be advantageous for the annotating if the second medical image data set uses all the image data set dimensions, whereas the first medical image data set has, for example, a reduced number of image data set dimensions. For example, the second medical image data set can have the time dimension, whereas the first medical image data set has e.g. an average over the time dimension, which in this example means that the first medical image data set has fewer image data set dimensions than the second medical image data set. The annotation, in particular of the clinically relevant structure, can preferably be performed more precisely by way of the time dimension, particularly if the clinically relevant structure contains the pulmonary nodule and/or the lymph node. The clinically relevant structure can in this case be annotated such that raw data for an inhalation and an exhalation of the patient is acquired, thereby creating the time dimension.

An embodiment provides that the first medical image data set has three image data set dimensions and the second medical image data set has four image data set dimensions. This embodiment is advantageous in that all the available image information can be used for annotating, particularly if the raw data is acquired in spatially and temporally resolved manner.

An embodiment provides that, in addition to the planning image rule, an annotation identifier is provided, wherein annotating the second medical image data set involves the annotation identifier in addition to the annotation instructions as input parameters, wherein the annotated image information contains the annotation identifier and wherein the annotation identifier contains a patient's tumor to be treated, a patient's organ at risk, an anatomical landmark of the patient and/or a patient's tissue to be classified. The annotation identifier is in particular provided by the user when providing the planning image rule e.g. by way of the display unit and/or the input device. The annotation identifier comprises in particular a selection as to the tumor to be treated, the organ at risk, the anatomical landmark and/or the tissue to be classified that are annotated in respect of the patient. The annotation identifier specifies in particular the anatomy, the clinically relevant structure of the patient, the implant and/or the anatomical landmark for annotation. The annotation identifier comprises in particular the clinical issue in question, which can preferably be taken into account in terms of annotation. The annotation rule, in particular the annotation instructions and/or the second reconstruction rule may depend in particular on the clinical issue in question.

An embodiment provides that the second medical image data set is annotated using an artificial neural network. The artificial neural network can in particular be trained for the visual impression of the second medical image data set, which can typically be distorted compared to the visual impression of the first medical image data set. The artificial neural network preferably allow faster annotation in this case. The artificial neural network typically has an input layer and an output layer, wherein the input layer and the output layer are usually linked via weighted connections. The weighted connections can have weighted edges between nodes in the input layer, in the output layer and/or in hidden layers between the input layer and the output layer. The artificial neural network can be a recurrent neural network which can be further developed and/or improved according to the annotated image information. The artificial neural network is typically trained using additional medical training image data sets and additional training annotated image information prior to annotating the second medical image data set. The annotating is typically carried out using the artificial neural network such that the second anatomical image data set and/or the annotation instructions are provided on the input layer, wherein the annotated image information is available on the output layer. It is basically conceivable for the annotation instructions to be represented in the weighted connections. The trained artificial neural network can be stored, for example, in the storage unit and/or in the buffer memory and/or in the main memory in particular prior to annotation.

A medical imaging unit according to at least one embodiment of the invention comprises a processing unit, wherein the medical imaging unit is designed according to at least one embodiment of the method for providing the annotated medical image data set for the patient's radiotherapy planning. The processing unit typically comprises a processor, a network connection, the main memory and/or the buffer memory.

A computer program product according to at least one embodiment of the invention, which can be loaded directly into a memory of the processing unit, has program code segments for carrying out at least one embodiment of the method for providing the annotated medical image data set for the patient's radiotherapy planning when the computer program product is executed in the processing unit.

The computer program product can be a computer program or comprise a computer program. The computer program product has in particular the program code segments which map the method steps according to at least one embodiment of the invention. As a result, the method according to the invention can be carried out in a definable and repeatable manner and control can be exercised over dissemination of the method according to at least one embodiment of the invention.

The computer program product is preferably configured such that the processing unit can carry out the method steps according to at least one embodiment of the invention using the computer program product. The program code segments can in particular be loaded into a memory of the processing unit and typically executed by way f a processing unit with access to the memory. When the computer program product, in particular the program code segments, is executed in the processing unit, typically the inventive embodiments of the method described can be carried out.

The computer program product is stored, for example, on a physical, computer-readable medium and/or in digital form as a data packet in a computer network. The computer program product can constitute the physical, computer-readable medium and/or the data packet in the computer network. Thus at least one embodiment of the invention can also proceed from the physical, computer-readable medium and/or the data packet in the computer network. The physical, computer-readable medium can usually be connected directly to the processing unit, e.g. by the physical, computer-readable medium being inserted in a DVD drive or plugged into a USB port, thereby providing the processing unit with, in particular, read access to the physical, computer-readable medium. The data packet can preferably be called up from the computer network. The computer network can contain the processing unit or be directly connected to the processing unit via a Wide Area Network (WAN) or a (Wireless) Local Area Network connection (WLAN or LAN). For example, the computer program product can be stored digitally on a cloud server at a storage location in the computer network, transferred via the WAN via the Internet and/or via the WLAN or LAN to the processing unit in particular by invoking a download link which indicates the storage location of the computer program product.

Features, advantages or alternative embodiments mentioned in the description of the apparatus are also applicable to the method and vice versa. In other words, claims for the method can also be further developed using features of the apparatus and vice versa. In particular, the apparatus according to the invention can be used in the method.

FIG. 1 shows a flow chart of the method for providing an annotated medical image data set for a patient's radiotherapy planning in a first example embodiment.

Method step S100 denotes providing an planning image rule for radiotherapy planning, comprising a scanning rule and a first reconstruction rule.

Method step S101 denotes retrieval of an annotation rule from a storage unit, wherein the annotation rule contains annotation instructions and a second reconstruction rule and wherein the second reconstruction rule is different from the first reconstruction rule.

Method step S102 denotes acquisition of the patient's raw data via a medical imaging unit in accordance with the scanning rule.

Method step S103 denotes reconstruction of a first medical image data set in accordance with the first reconstruction rule using the raw data.

Method step S104 denotes reconstruction of a second medical image data set in accordance with the second reconstruction rule using the raw data.

Method step S105 denotes annotating of the second medical image data set in accordance with the annotation instructions, wherein annotated image information is determined.

Method step S106 denotes combining of the first medical image data set with the annotated image information, wherein an annotated medical image data set is produced.

Method step S107 denotes providing the annotated medical image data set for the patient's radiotherapy planning.

Figure 2:
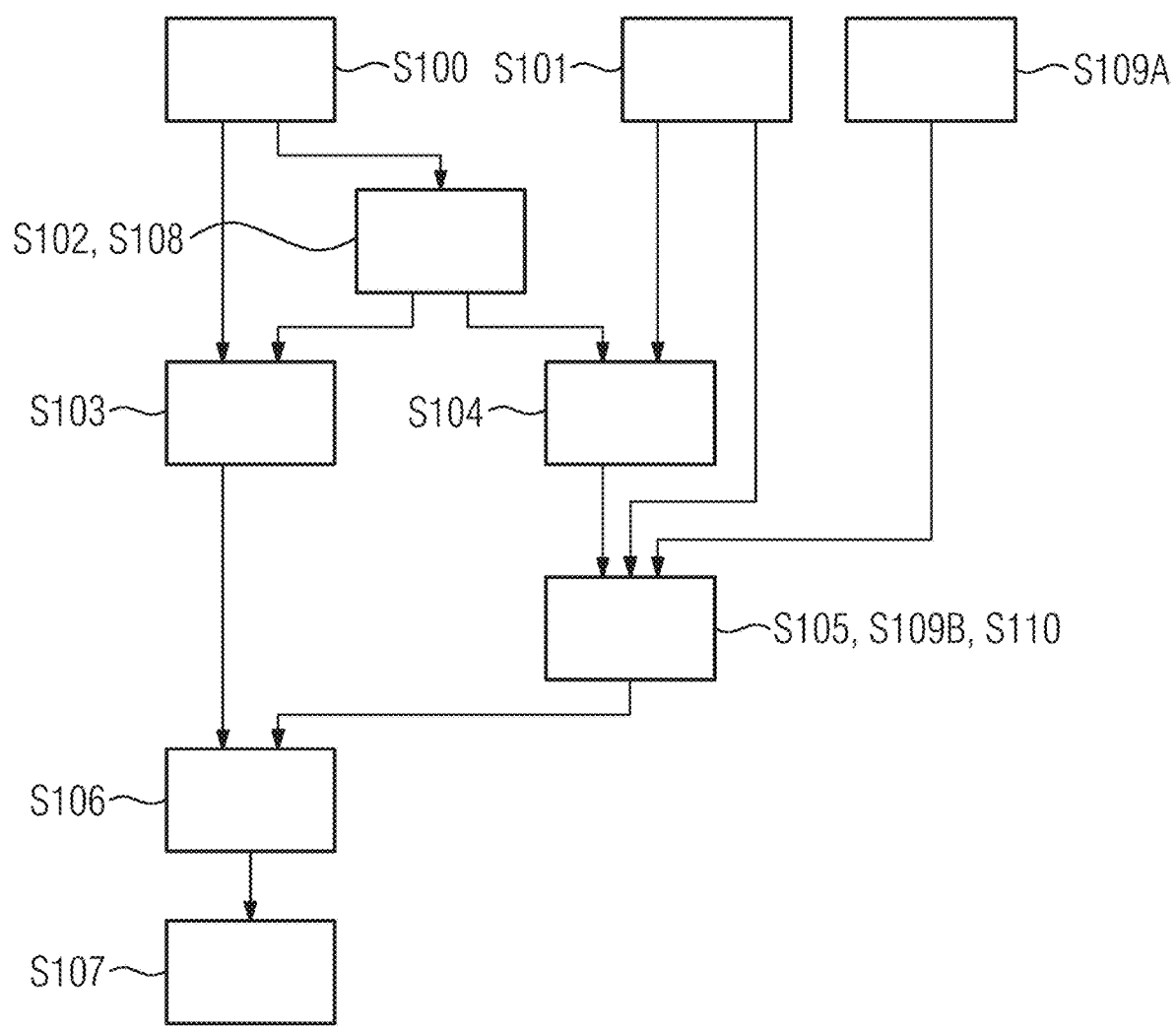
FIG. 2 shows the method in a second example embodiment and FIG. 3 shows a medical imaging unit in a third example embodiment.

FIG. 2 shows the method in a second example embodiment, wherein one or more of the method steps added compared to FIG. 1 can basically be omitted in another example embodiment.

Method step S108 denotes that the scanning rule is a multi-energy scanning rule for acquiring spectrally resolved raw data, wherein the first reconstruction rule differs from the second reconstruction rule in respect of weighting of the spectrally resolved raw data.

Method step S109A denotes that an annotation identifier is provided in addition to the planning image rule.

Method step S109B denotes that annotating the second medical image data set involves the annotation identifier in addition to the annotation instructions as input parameters, wherein the annotated image information contains the annotation identifier and wherein the annotation identifier includes a patient's tumor to be treated, a patient's organ at risk, a patient's anatomical landmark and/or a patient's tissue to be classified.

Method step S110 denotes that the second medical image data set is annotated using an artificial neural network.

Figure 3:
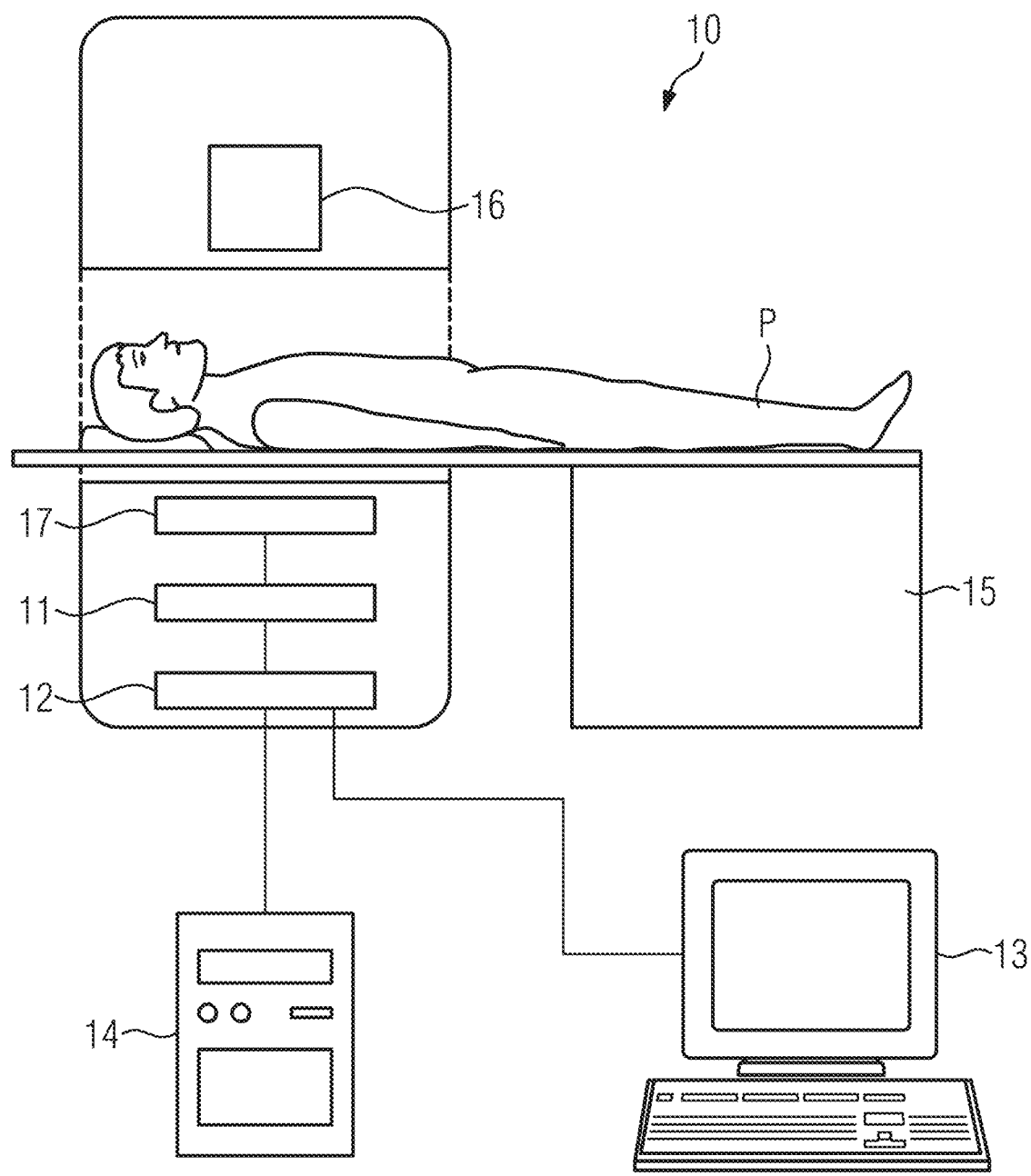

FIG. 3 shows the medical imaging unit 10 in a third example embodiment. The medical imaging unit 10 comprises the processing unit (including at least one processor) 11, a memory including at least a buffer memory 12 and a display unit 13 with input device(s) for a user. The medical imaging unit 10, in particular the buffer memory 12, is connected to a storage unit 14. The user can provide a planning image rule for radiotherapy planning via the display unit 13. The planning image rule and the annotation rule are together stored in the buffer memory 12, in particular until retrieval for acquiring the raw data and/or for reconstructing the first medical image data set and/or for reconstructing the second medical image data set and/or for annotating the second medical image data set. The buffer memory 12 can be implemented as a main memory of the processing unit 11. The buffer memory 12 and the processing unit 11 can be designed for combining the first medical image data set with the annotated image information and/or for providing the annotated medical image data set. The medical imaging unit 10 is designed to retrieve an annotation rule from the storage unit 14 and to temporarily store the annotation rule in the buffer memory 12, in particular via the processing unit 11. The patient P is positioned on a patient table 15 in particular for acquiring the raw data. The annotated medical image data set is provided on the display unit 13 for the radiotherapy planning of the patient P preferably by the processing unit 11 and/or the buffer memory 12.

A radiotherapy system for performing radiotherapy in accordance with the radiotherapy planning is not shown in FIG. 3. The radiotherapy can be carried out according to various radiotherapy methods. It is basically conceivable for the medical imaging unit 10 to comprise the radiotherapy system.

In this example embodiment, the medical imaging unit 10 is implemented as a CT scanner and has an X-ray source 16 and an X-ray detector 17 for acquiring the raw data, which can typically be controlled by the processing unit. Alternatively or in addition, the medical imaging unit 10 can be implemented as an MRI scanner comprising a main magnetic field unit and a gradient magnetic field unit.

Although the invention has been illustrated and described in detail by the preferred example embodiments, the invention is, however, not limited by the examples disclosed and other variations will be apparent to persons skilled in the art without departing from the scope of protection sought for the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing an annotated medical image data set for radiotherapy planning of a patient, comprising:
providing a planning image rule for the radiotherapy planning, including a scanning rule and a first reconstruction rule;
retrieving an annotation rule from storage, the annotation rule containing annotation instructions and a second reconstruction rule, the second reconstruction rule being different from the first reconstruction rule;

acquiring raw data of the patient via a medical imaging device in accordance with the scanning rule;

reconstructing a first medical image data set in accordance with the first reconstruction rue using the raw data acquired;

reconstructing a second medical image data set in accordance with the second reconstruction rule using the raw data acquired;

annotating the second medical image data set in accordance with the annotation instructions, to determine annotated image information;

transferring the annotated image information from the second medical image data set to first medical image data set;

combining the first medical image data set with the transferred annotated image information by overlaying the annotated image information on the first medical image data set, to produce the annotated medical image data set; and providing the annotated medical image data set for radiotherapy planning of the patient;

wherein a filter of the second reconstruction rule differs from a filter of the first reconstruction rule such that image edges in the second medical image data set are mapped in a relatively more contoured manner than image edges in the first medical image data set.

2. The method of claim 1, wherein an artifact correction method of the first reconstruction rule differs from an artifact correction method of the second reconstruction rule such that, after application of the artifact correction method, a number of image artifacts in the second medical image data set is relatively less in number than a number of image artifacts in the first medical image data set.

3. The method of claim 1, wherein a fidelity of reproduction of material properties of the first reconstruction rule is relatively higher than a fidelity of reproduction of the material properties of the second reconstruction rule.

4. The method of claim 1, wherein a sure thickness of the second reconstruction rule is relatively less than a slice thickness of the first reconstruction rule.

5. The method of claim 1, wherein a reconstruction volume of the second reconstruction rule is relatively greater than a reconstruction volume of the first reconstruction rule.

6. The method of claim 1, wherein the first reconstruction rule differs from the second reconstruction rule such that an image resolution in the second medical image data set is relatively higher than an image resolution in the first medical image data set.

7. The method of claim 1, wherein the second reconstruction rule contains reference value specifications and wherein the reference value specifications are taken into account for reconstructing the second medical image data set, such that a contrast of the first medical image data set differs from a contrast of the second medical image data set.

8. The method of claim 7, wherein the reference value specifications contain a CT number for an organ of the patient.

9. The method of claim 1, wherein the scanning rule comprises a multi-energy scanning rule for acquiring spectrally resolved raw data and wherein the first reconstruction rule differs from the second reconstruction rule in respect of weighting of the spectrally resolved raw data acquired.

10. The method of claim 1, wherein the first reconstruction rule differs from the second reconstruction rule, the first medical image data set and the second medical image data set having different image data set dimensions.

11. The method of claim 10, wherein the first medical image data set has three image data set dimensions and the second medical image data set has four image data set dimensions.

12. The method of claim 1, wherein, in addition to the planning image rule, an annotation identifier is provided, wherein the annotating of the second medical image data set involves using the annotation identifier and the annotation instructions as input parameters, wherein the annotated image information contains the annotation identifier and wherein the annotation identifier references at least one of a tumor of the patient to be treated, an organ of the patient at risk, an anatomical landmark of the patient and a tissue of the patient to be classified.

13. The method of claim 1, wherein the second medical image data set is annotated using an artificial neural network.

14. A medical imaging unit, comprising: a memory storing executable instructions; and at least one processor, the at least one processor being, upon execution of the executable instructions, configured to:

provide a planning image rule for radiotherapy planning of a patient, including a scanning rule and a first reconstruction rule;

retrieve an annotation rule from storage, the annotation rule containing annotation instructions and a second reconstruction rule, the second reconstruction rule being different from the first reconstruction rule;

acquire raw data of the patient, via a medical imaging device, in accordance with the scanning rule;

reconstruct a first medical image data set in accordance with the first reconstruction rule using the raw data acquired; reconstruct a second medical image data set in accordance with the second reconstruction rule using the raw data acquired;

annotate the second medical image data set in accordance with the annotation instructions, to determine annotated image information;

transfer the annotated image information from the second medical image data set to first medical image data set;

combine the first medical image data set with the transferred annotated image information annotated image information by overlapping the annotated image information on the first medical image data set, to produce an annotated medical image data set; and provide the annotated medical image data set for the radiotherapy planning of the patient;

wherein a filter of the second reconstruction rule differs from a filter of the first reconstruction rule such that image edges in the second medical image data set are mapped in a relatively more contoured manner than image edges in the first medical image data set.

15. The medical imaging unit of claim 14, further comprising: the medical imaging device, including an X-ray source and an X-ray detector, to acquire the raw data.

16. The medical imaging unit of claim 14, further comprising: the medical imaging device implemented as an MRI scanner, including a main magnetic field unit and a gradient magnetic field unit.

17. The medical imaging unit of claim 14, further comprising: a display, to display the annotated medical image data set for the radiotherapy planning of the patient.

18. A non-transitory computer readable medium, storing program code segments for, upon the program code segments being executed by a processor:

providing a planning image rule for radiotherapy planning of a patient, including a scanning rule and a first reconstruction rule; retrieving an annotation rule from storage, the annotation rule containing annotation instructions and a second reconstruction rule, the second reconstruction rule being different from the first reconstruction rule;

acquiring raw data of the patient via a medical imaging device in accordance with the scanning rule; reconstructing a first medical image data set in accordance with the first reconstruction rule using the raw data acquired; reconstructing a second medical image data set in accordance with the second reconstruction rule using the raw data acquired;

annotating the second medical image data set in accordance with the annotation instructions, to determine annotated image information;

transferring the annotated image information from the second medical image data set to first medical image data set;

combining the first medical image data set with the transferred annotated image information annotated image information by overlapping the annotated image information on the first medical image data set, to produce an annotated medical image data set; and providing the annotated medical image data set for the radiotherapy planning of the patient;

wherein a filter of the second reconstruction rule differs from a filter of the first reconstruction rule such that image edges in the second medical image data set are mapped in a relatively more contoured manner than image edges in the first medical image data set.

19. The non-transitory computer readable medium of claim 18, wherein the processor, upon the program code segments being executed, is further configured to perform the annotating of the second medical image data set using an artificial neural network.

* * * * *